United States Patent

Typpo

[11] Patent Number: 4,791,353
[45] Date of Patent: Dec. 13, 1988

[54] SCANNING COMBINATION THICKNESS AND MOISTURE GAUGE FOR MOVING SHEET MATERIAL

[75] Inventor: Pekka Typpo, Cupertino, Calif.
[73] Assignee: Impact Systems, Inc., San Jose, Calif.
[21] Appl. No.: 85,443
[22] Filed: Aug. 14, 1987
[51] Int. Cl.[4] ............................................. G01R 27/26
[52] U.S. Cl. .................................. 324/61 R; 324/61 P
[58] Field of Search ...................... 324/61 R, 229, 230, 324/231, 61 P; 340/602

[56] References Cited

U.S. PATENT DOCUMENTS

| | | | |
|---|---|---|---|
| 3,258,686 | 6/1966 | Selgin | 324/230 |
| 3,523,243 | 8/1970 | Wagner | 324/61 R |
| 4,675,595 | 6/1987 | Hane | 324/58.5 R |

FOREIGN PATENT DOCUMENTS 393656 12/1971 U.S.S.R. ............................ 324/61 R

Primary Examiner—Reinhard J. Eisenzopf
Assistant Examiner—Anthony L. Miele
Attorney, Agent, or Firm—Flehr, Hohbach, Test, Albritton & Herbert

[57] ABSTRACT

A combination caliper/moisture sensor in the form of a scanner in the cross-direction of sheet material being manufactured by a papermaking machine includes a pair of capacitive plates on opposite sides of the moving sheet material and in substantial contact with it which are utilized for measuring capacitance between the juxtaposed plates which are spaced in accordance with the caliper of the paper. Then a magnetic circuit which provides a flux path through the paper is utilized for measuring caliper which is the independent variable of the capacitance equation which, when solved, yields the dielectric constant. Since there is a known relationship between percent moisture and the dielectric constant, the percent moisture of the sheet material can be determined.

3 Claims, 3 Drawing Sheets

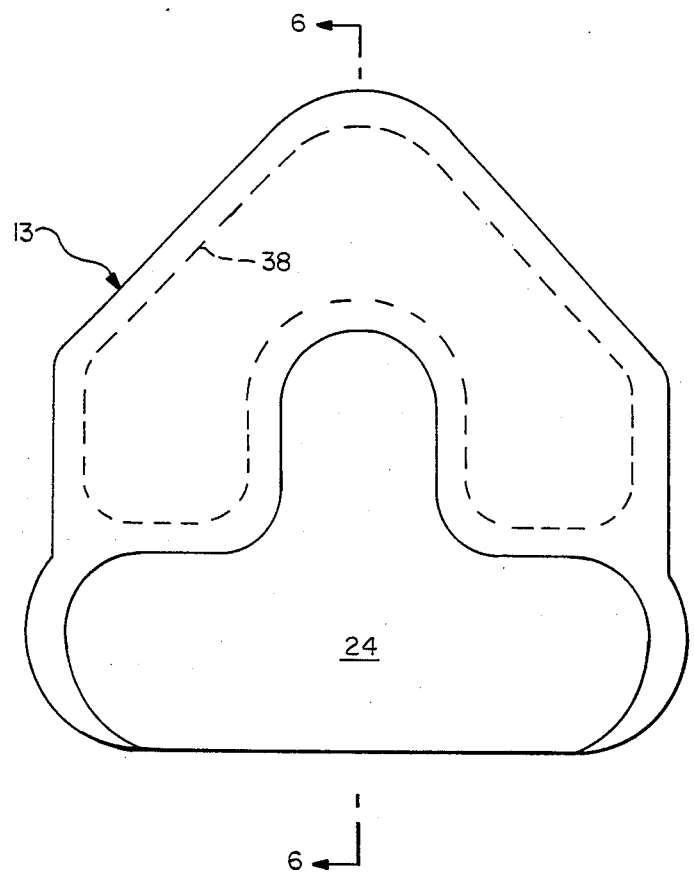
FIG.—5
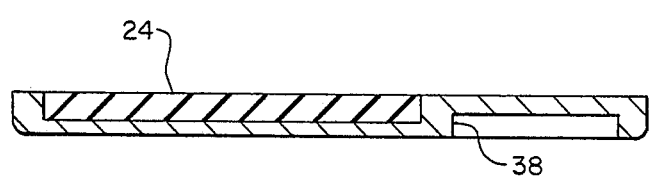
FIG.—6

4,791,353

SCANNING COMBINATION THICKNESS AND MOISTURE GAUGE FOR MOVING SHEET MATERIAL

BACKGROUND OF THE INVENTION

The present invention is directed to a scanning combination thickness and moisture gauge for moving sheet material. The thickness gauge portion is disclosed and claimed in a co-pending application in the name of Pekka Typpo entitled "Contacting Thickness Gauge for Moving Sheet Material" filed July 15, 1987, Ser. No. 073,734, which is hereby incorporated by reference.

DESCRIPTION OF PRIOR ART

The measurement of moisture in a moving web of, for example, paper, is presently commonly done by a scanning type moisture sensor utilizing an infrared frequency signal which is sensitive to moisture in the paper. This method requires a finely adjusted optical path, along with associated electronics for standardization. However, it is a highly accurate method.

Capacitance type moisture type sensors are also utilized, as illustrated, for example, in U.S. Pat. No. 3,408,566 which has a pair of capacitive plates but on one side of the moving sheet material. The accuracy of a simple capacitive type of moisture gauge, as above, is not as great as desired relative to the infrared type gauge.

OBJECT AND SUMMARY OF THE INVENTION

It is therefore a general object of the present invention to provide an improved moisture gauge for moving sheet material of the capacitive plate type.

In accordance with the above object, there is provided a scanning combination thickness and moisture gauge for moving sheet material comprising a pair of conductive plate means adapted for substantially contacting opposite sides of the moving sheet material and forming a capacitor whose capacitance depends on the moisture in the sheet material and is inversely proportional to the thickness (caliper) of the sheet material between the plate means. Means are provided for measuring this capacitance. Magnetic means integrally associated with the plate means provide a magnetic flux path through the sheet material for measuring its thickness. And then electrical processing means are responsive to the measured capacitance and thickness for determining moisture.

BRIEF DESCRIPTION OF DRAWINGS

FIG. 5 is a plan view of a portion of the passive magnetic means embodying the present invention.

FIG. 6 is a cross-sectional view taken along lines 6—6 of FIG. 5.

DESCRIPTION OF PREFERRED EMBODIMENT

Figure 1:
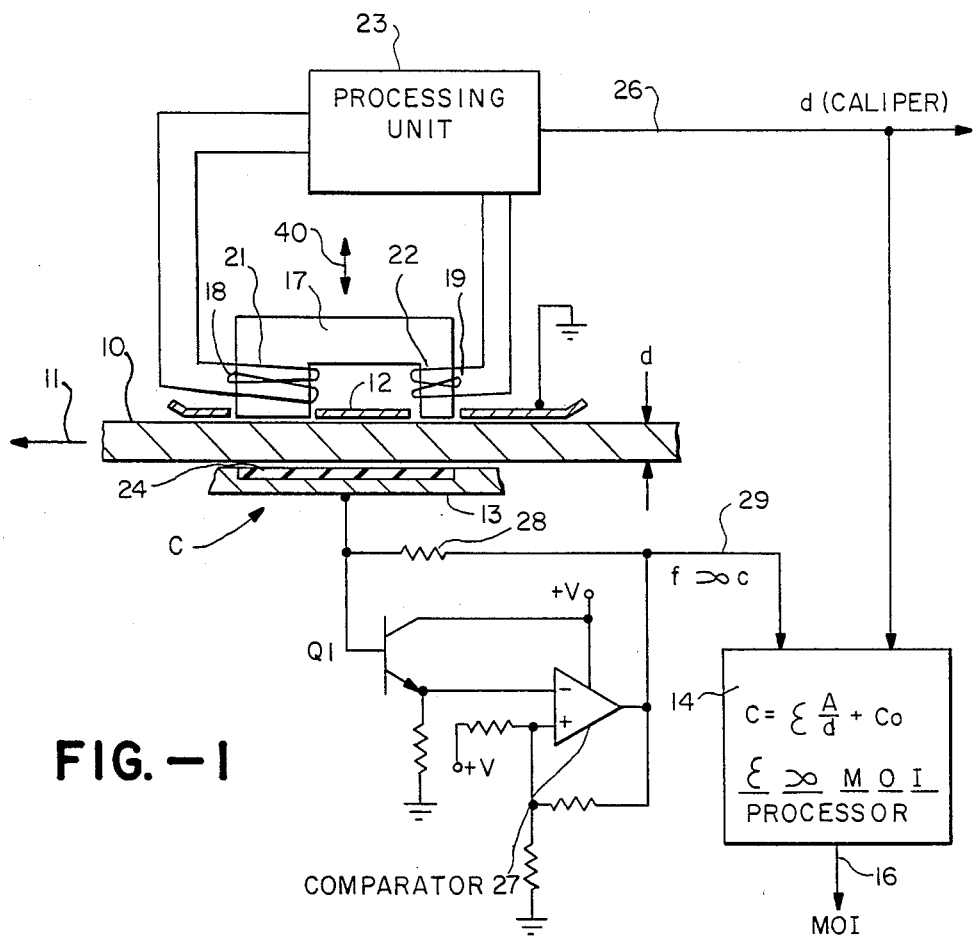
FIG. 1 is a cross-sectional view of the apparatus of the present invention showing its use on moving sheet material, along with a circuit schematic and block diagram of associated circuitry.

FIG. 1 illustrates the overall layout of the present invention showing how it is applied to moving sheet material 10, as it would be manufactured on a paper machine which is moving in the direction indicated by the arrow 11. Paper 10, of course, as it is being manufactured, has a certain thickness (more commonly termed in the industry "caliper") designated 'd,' and carries varying amounts of moisture, usually designated as 'percent moisture.' In order to provide feedback control signals for various actuators on the papermaking machine, it is necessary to sense both caliper and percent moisture of the various "slices" of the paper.

Figure 2:
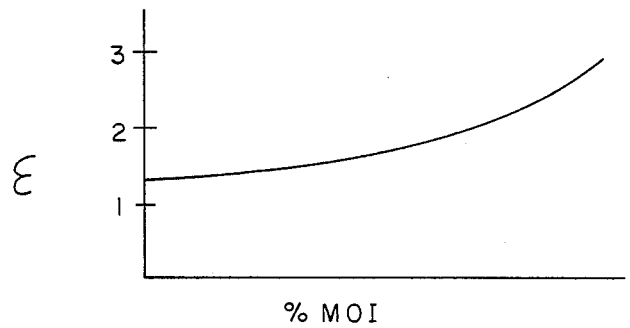
FIG. 2 is a characteristic curve useful in understanding the invention.

In general, the gauge incorporating the present invention includes a pair of parallel conductive plates 12 and 13, which substantially contact opposite sides of moving sheet 10 and form a capacitor designated by the letter C. This capacitance is proportional to both the moisture content of the sheet material and its caliper, d. More specifically, as illustrated in the processor block 14, the equation for capacitance C lists in this instance the dielectric constant between the plates, E, multiplied by the ratio of the electrode area, A, and the caliper d. And then the term $C_0$ is the stray capacitance. As illustrated in FIG. 2 and also in processor box 14 (which may be a microprocessor), the dielectric constant is proportional to percent moisture in the manner shown. Thus, a determination of the dielectric constant by processor 14 and a knowledge of the relatively constant curve of FIG. 2 will yield the percent moisture on the output line 16.

However, it is apparent looking at the equation of block 14 that capacitance has as an independent variable the caliper d. In order to obtain this caliper there is integrally mounted to the capacitor plates 12 and 13 magnetic means for providing a magnetic flux through the sheet material for measuring caliper. This includes a U-shaped pole piece 17 having legs 18 and 19 with the ends of the these legs terminating in plate 12 and juxtaposed with one side of the sheet material 10. Wrapped around each leg 18 and 19 are coils 21 and 22 which, when appropriately energized and controlled by a processing unit 23, provide a magnetic flux from the end of one leg through a passive magnetic means in the form of a ferrite slab 24, which is inset in the top of capacitive plate 13 on the opposite side of sheet material 10. This passive plate 24 thus completes the flux path from the active magnetic means through the sheet material.

Appropriate measurement of the reluctance of this flux path provides the output of processing unit 23 on the line 26 which is a signal indicative of caliper. While any type of integral magnetic means on one side or both sides of the paper will provide measurement of caliper (and is suitable for the present invention), it is believed the preferred technique is shown in FIG. 1 and also as disclosed and claimed in the above co-pending Typpo application. Briefly, this technique utilizes the mutual inductance between the coils 18 and 19 for providing a measurement of caliper.

For measuring the capacitance C between the plates 12 and 13, there is provided a relaxation oscillator of the RC type connected between plate 13 and ground which is formed by plate 12. This includes the transistor Q1 with its base input driven by the signal on plate 13. Transistor Q1 drives the negative polarity input of a comparator 27, which has a feedback path including resistor 28. On the output line 29, there is a signal having a frequency proportional to capacitance. This is coupled into processor unit 14 along with caliper, to thus provide the dielectric constant (assuming stray capacitance $C_0$ is substantially constant) which when utilized with the curve of FIG. 2, provides percent moisture on output line 16.

Ferrite slab 24, which is the passive magnetic means inset in plate 13, has a dielectric constant of greater than 10. This makes it electrically transparent to the overall measurement of capacitance, since the dielectric constant of paper, as shown in FIG. 2, may range from 1 to 3. For example, the dielectric constant of bone dry newsprint is approximately 1.4 and with 10% moisture, is 2.4. Thus, the dielectric slabs can be regarded as part of a series capacitive circuit with the lowest "resistance" component being negligible in comparison with the higher one. Thus, in essence, the additional dielectric components needed for measurement of caliper have no effect on the sensitivity of the capacitance measurement.

Figure 3:
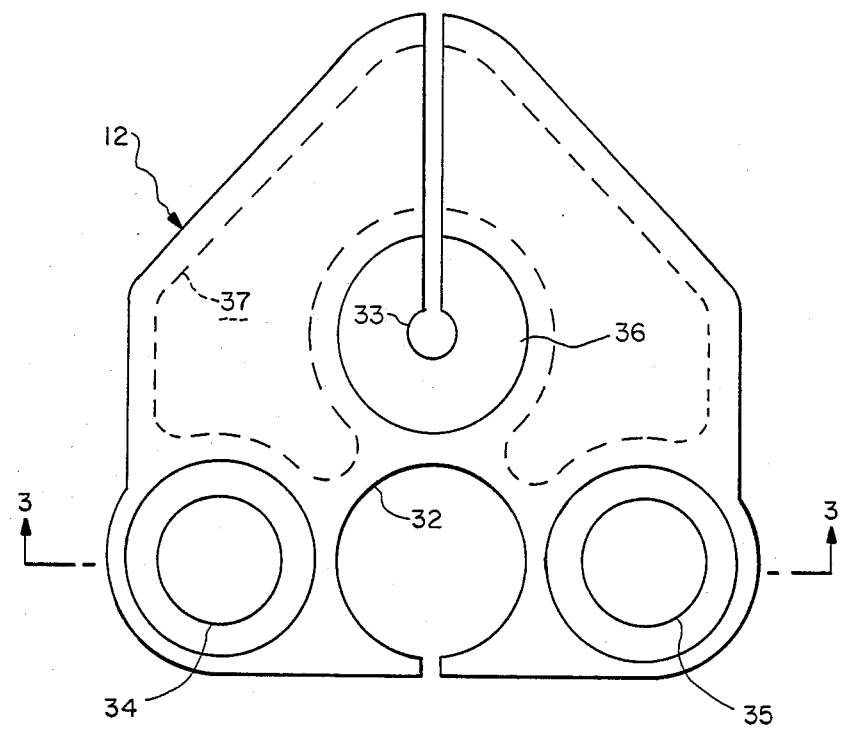
FIG. 3 is a plan view of a portion of the active magnetic means embodying the present invention.
Figure 4:
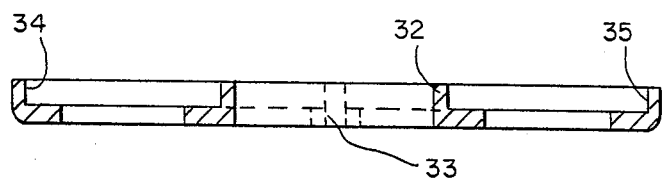
FIG. 4 is a cross-sectional view taken along line 3—3 of FIG. 3.

The specific optimal configuration of the plates 12 and 13 is respectively illustrated in FIGS. 3 and 5, with associated cross-sectional views in FIGS. 4 and 6. These plates are very similar to those shown in the above Typpo co-pending application.

Referring to FIG. 3 plate 12 is made of titanium metal and has a large cutout 32 for the leg 18 and a smaller cutout 33 for the leg 19, as illustrated in FIG. 1. As described more fully in the above co-pending Typpo application, jewel-type bearings are inserted for a three point pivot at 34, 35 and 36. To provide for light weight there is a recess 37 indicated by the dashed portion. As also described in the above Typpo application, rather than jewel bearings, air bearings could be utilized. In actual practice, the smaller leg 19 is in contact with the paper whereas the larger leg 18 is held slightly off the paper by the jewel bearings at 34 and 35. However, this is in controlled and fixed proximity to the paper; in essence, it amounts to substantial contact.

The passive magnetic means, including the capacitive plate 13, is illustrated in FIG. 5, where the ferrite plate 24, as shown in FIG. 6 is inset into the recess of the plate.

There is also a hollowed out recess indicated by dashed lines 38 for weight reduction. A typical dimension of the thickness of the ferrite slab 24 is approximately 0.060 inches.

Finally, as shown in the above Typpo application, the pair of capacitor plates 12 and 13 are suspended on trailing arms which extend to scanner unit which provides for cross-direction scan in the direction as indicated by the double ended arrow 40 (FIG. 1) across the machine direction 11 of the paper.

Thus, an improved combination caliper-moisture gauge has been provided.

I claim:

1. A scanning combination thickness and moisture gauge for moving sheet material comprising:
   a pair of conductive plate means adapted for substantially contacting opposite sides of said moving sheet material and forming a capacitor whose capacitance is proportional to moisture in said sheet material and inversely proportional to thickness (caliper) of said sheet material between said plate means;
   means for measuring said capacitance;
   magnetic means integrally associated with said plate means for providing a magnetic flux path through said sheet material for measuring said thickness including passive magnetic means, carried by one of said pairs of plate means, for forming a part of said magnetic flux path; and
   electrical processing means responsive to said measured capacitance and thickness for determining said moisture.

2. A gauge as in claim 1 where said magnetic means comprises active magnetic means including a U-shaped pole piece having two legs with ends each of them terminating in an aperture in the other of said pair of plate means.

3. A gauge as in claim 1 where said passive magnetic means has a dielectric constant greater than 10 to make it electrically transparent to said measurement of said capacitance.

* * * * *